US007012165B2

(12) United States Patent
Dolbier, Jr. et al.

(10) Patent No.: US 7,012,165 B2
(45) Date of Patent: Mar. 14, 2006

(54) OXIDATIVE FLUORINATION OF AROMATIC AND CHLOROAROMATIC DERIVATIVES

(75) Inventors: William R. Dolbier, Jr., Gainesville, FL (US); Buvaneswari Gopal, Gainesville, FL (US)

(73) Assignee: University of Florida, Gainesville, FL (US)

( * ) Notice: Subject to any disclaimer, the term of this patent is extended or adjusted under 35 U.S.C. 154(b) by 229 days.

(21) Appl. No.: 10/698,110

(22) Filed: Oct. 31, 2003

(65) Prior Publication Data

US 2005/0096489 A1    May 5, 2005

(51) Int. Cl.
*C07C 19/08* (2006.01)
*C07C 17/00* (2006.01)
*C07D 211/72* (2006.01)

(52) U.S. Cl. ...................... 570/127; 570/147; 570/163; 546/345

(58) Field of Classification Search ................ 570/127, 570/147, 163; 546/345
See application file for complete search history.

(56) References Cited

U.S. PATENT DOCUMENTS 6,087,543 A    7/2000    Subramanian
6,166,273 A    12/2000   Subramanian

*Primary Examiner*—Johann Richter
*Assistant Examiner*—Sikarl A. Witherspoon
(74) *Attorney, Agent, or Firm*—Saliwanchik, Lloyd & Salinwanchik

(57) ABSTRACT

The subject invention provides methods of fluorinating an aromatic or chloroaromatic compound comprising combining an aromatic compound, a chloroaromatic compound, a mixture of aromatic compounds, a mixture of chloroaromatic compounds, or a mixture of chloroaromatic and aromatic compounds and a fluorinating composition comprising at least one active fluorinating agent selected from the group consisting of $CuF_2$, $AgF$, $HgF_2$, $TeF_4$, $MnF_4$, $FeF_3$, and $CoF_{2-4}$ and at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$.

37 Claims, No Drawings

OXIDATIVE FLUORINATION OF AROMATIC AND CHLOROAROMATIC DERIVATIVES

BACKGROUND

Fluorobenzene, a chemical used to control carbon content in steel manufacturing or an intermediate for pharmaceuticals, pesticides and other organic compounds, is typically produced by the reaction of aniline and sodium nitrite in the presence of hydrogen fluoride.

U.S. Pat. Nos. 6,087,543 and 6,166,273 provide improved methods for the fluorination of aromatic ring compounds or benzene. However, these patents provide relatively low yields of desired compounds. Accordingly, there is still a need for efficient commercial processes for preparing fluorobenzene or, more generally, fluorinating compounds having a benzene nucleus using less expensive materials.

SUMMARY OF THE INVENTION

The subject invention provides methods of fluorinating an aromatic or chloroaromatic compound comprising combining an aromatic compound, a chloroaromatic compound, a mixture of aromatic compounds, a mixture of chloroaromatic compounds, or a mixture of chloroaromatic and aromatic compounds and a fluorinating composition comprising at least one active fluorinating agent selected from the group consisting of $CuF_2$, $AgF$, $HgF_2$, $TeF_4$, $MnF_4$, $FeF_3$, and $CoF_{2-4}$ and at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$. Aromatic and chloroaromatic compounds that are to be fluorinated can be substituted with a variety of inert substituents. In certain embodiments, the compounds are substituted with 1, 2, or 3 inert substituents. We have, unexpectedly, found that contacting aromatic or chloroaromatic compounds with a mixture of metal fluorides results in an increased yield of fluorinated compounds.

DETAILED DESCRIPTION

In a first embodiment, the subject invention provides a method of fluorinating an aromatic or chloroaromatic compound comprising combining an aromatic compound, a chloroaromatic compound, a mixture of aromatic compounds, a mixture of chloroaromatic compounds, or a mixture of chloroaromatic and aromatic compounds and a fluorinating composition comprising at least one active fluorinating agent selected from the group consisting of $CuF_2$, $AgF$, $HgF_2$, $TeF_4$, $MnF_4$, $FeF_3$, and $CoF_{2-4}$ and at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$ and heating the combined components to a temperature of at least 350° C. Optionally, fluorinated aromatic or chloroaromatic compounds are then recovered from the reaction mixture.

A second embodiment of the subject invention provides methods of fluorinating an aromatic compound comprising the steps of:

a) mixing at least one active fluorinating agent selected from the group consisting of $CuF_2$, $AgF$, $HgF_2$, $TeF_4$, $MnF_4$, $FeF_3$, and $CoF_{2-4}$ with at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$;

b) heating said mixture to a temperature of at least 350° C.; and c) contacting said mixture with an aromatic compound, a chloroaromatic compound, a mixture of aromatic compounds, a mixture of chloroaromatic compounds, or a mixture of chloroaromatic and aromatic compounds and, optionally, recovering fluorinated aromatic or chloroaromatic compounds.

In either of the foregoing embodiments, the mixture of compounds can be heated to temperatures of at least 400° C., at least 425° C., at least 450° C., or at least 500° C. Aromatic or chloroaromatic compounds for use in either method can be one compound, or any combination of compounds, selected from the group consisting of benzene, chlorobenzene, substituted benzene, substituted chlorobenzene, pyridines, chloropyridines, substituted pyridines, substituted chloropyridines, naphthalene, substituted naphthalenes, chloronapthalene, substituted chloronaphthalenes, toluene, chlorotoluene, substituted toluene, and substituted chlorotoluene. As indicated supra, aromatic and chloroaromatic compounds can be substituted with any number of inert substituents. In certain embodiments, the compounds are substituted with 1, 2, or 3 inert substituents.

The methods of the subject invention utilize fluorinating compositions that comprise at least one active fluorinating agent selected from the group consisting of $CuF_2$, $AgF$, $HgF_2$, $TeF_4$, $MnF_4$, $FeF_3$, and $CoF_{2-4}$ and at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$. In certain embodiments of the subject invention, the fluorinating composition comprises $CuF_2$ and $AgF$ in various ratios. These ratios can be manipulated such that the fluorinating composition is pure $CuF_2$ or pure $AgF$. Alternatively, the fluorinating compositions can comprise various ratios of $CuF_2$ and $AgF$. In various embodiments of the subject invention, fluorinating compositions containing $AgF$ is used to fluorinate chloroaromatic compounds. In other embodiments of the invention, fluorinating compositions comprising $CuF_2$ is used to fluorinate aromatic hydrocarbons.

A process is also provided for increasing the fluorine content of an aromatic ring compound or a chloroaromatic ring compound (e.g., a benzene ring, a pyridine ring, a benzene ring substituted with from 1 to 3 inert substituents and a pyridine ring substituted with from 1 to 3 inert substituents). The process comprises (a) contacting the ring compound with a metal fluoride composition comprising $CuF_2$ and/or $AgF$ and another metal fluoride (a support) at a temperature above 300° C. Such temperatures are sufficient to transfer fluorine atoms to the aromatic ring, thereby chemically reducing the metal fluoride composition; (b) oxidizing the reduced metal fluoride composition from (a) in the presence of HF to regenerate a metal fluoride composition comprising $CuF_2$ and/or $AgF$; and (c) employing regenerated metal fluoride composition of (b) in (a).

Oxidative fluorination of aromatic compounds using transition metal fluorides is schematically represented below.

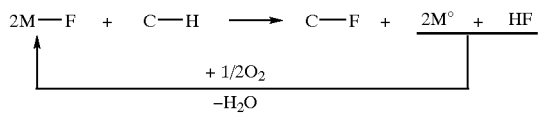

With the simple metal fluorides, the fluorinating power depends on the redox potentials of the metal ions involved. Fluorides of the metal ions with $E^0>1$ are very strong fluorinating agents giving rise to saturated products. Fluorides of the metal ions with $E^0<0$ are inert towards aromatics. On the other hand, fluorides of the metal ions with $1>E^0>0$ are mild fluorinating agents. Metal fluorides useful as mild fluorinating agents in the present invention include but are not limited to $CuF_2$, $AgF$, $HgF_2$, and $Hg_2F_2$. As illustrated in the examples attached hereto, a 73% conversion of benzene to fluorobenzene and difluorobenzene (ratio of fluorobenzene to difluorobenzene=88:12) was obtained when benzene was contacted with a mixture of $CuF_2$ and $AlF_3$ ($CuF_2$:$AlF_3$ ratio=1:2) at a temperature of 500° C. At temperatures of 450° C., 44.3% conversion of benzene to fluorobenzene and difluorobenzene was observed (with a fluorbenzene:diflorobenzene ratio of 91:9). At 400° C., fluorobenzene was formed selectively with a yield of 24%. The use of $CaF_2$ or $MgF_2$ provided similar results to the use of $AlF_3$.

As is also illustrated in the examples, chlorobenzene can be converted to a mixture of fluorobenzene, difluorobenzene, and chlorofluorobenzene when reacted with mixtures of $CuF_2$ and $AlF_3$ (ratio of 1:2). At temperatures of 500° C., chlorobenzene is converted to fluorobenzene, difluorobenzene, and chlorofluorobenzene at a ratio of 85:7:9 (with a yield of 65%).

Additionally, we have found that ortho-, meta-, and para-chlorotoluenes can be converted to mixtures of fluorotoluenes when reacted with AgF at temperatures of at least about 350° C. with conversion yields of 29%, 47%, and 57% respectively. Ortho- and meta-dichlorobenzenes are converted to meta-difluorobenzene (12% and 20% conversion respectively) plus chlorofluorobenzene (6.7% and 14.5% respectively). All chlorofluorobenzenes exhibited conversion to one product (meta-fluorobenzene) under the reaction conditions.

Following are examples that illustrate procedures for practicing the invention. These examples should not be construed as limiting. All percentages are by weight and all solvent mixture proportions are by volume unless otherwise noted.

EXAMPLE 1

Fluorination of Benzene Utilizing $AlF_3$ and $CuF_2$ as the Fluorinating Agent

Anhydrous $AlF_3$ (ALFAAESAR, 99.5%) and anhydrous $CuF_2$ (ALFAAESAR, 99.5%) were used. To a weighed amount of $CuF_2$, $AlF_3$ (~35 mesh size) was mixed in different ratios (1:1, 1:1.5, 1:2, 1:2.5, 1:3). In a typical fluorination experiment, the metal fluoride mixture was loaded into a hastelloy reactor tube in a dry box. The reactor tube was heated to 500° C. under a flow of Ar gas. The flow rate of the carrier gas was adjusted to 25 mL/min. Vaporized benzene was passed over the heated fluoride mixture. The duration of the reaction was about 1½ to 2½ hrs. At the end of the reaction, the reactor tube was swept out with the carrier gas. The organic product was analyzed using HP 6890 GC/5973 Mass Spectrometer. The inorganic residue was analyzed by powder X-ray diffractometer (XRD PHILIPS APD 3720).

Percentage conversions of benzene to the fluorinated products, m-fluorobenzene, flurobenzene, and o-fluorobenzene, where the amount of $AlF_3$ increases and $CuF_2$ remains constant are given in Table 1.

TABLE 1

| | | Products | | |
| --- | --- | --- | --- | --- |
| Fluoride Mixture | Temperature (° C.) | m-difluorobenzene | fluorobenzene | o-difluorobenzene |
| $CuF_2$(3.5 g) + $AlF_3$ 1:1 | 500 | — | 19.7 | 0.8 |
| $CuF_2$(3.5 g) + $AlF_3$ 1:1.5 | 500 | — | 32.7 | 0.9 |
| $CuF_2$(3.5 g) + $AlF_3$ 1:2 | 500 | 2.4 | 48.1 | 1.6 |
| $CuF_2$(3.5 g) + $AlF_3$ 1:2.5 | 500 | — | 40.1 | 1.0 |
| $CuF_2$(3.5 g) + $AlF_3$ 1:3 | 500 | — | 28.6 | 1.0 |

On the basis of the above results, the ratio of $CuF_2$ to $AlF_3$ was fixed as 1:2, and additional experiments were carried out at 450° C. and 425° C. The results are given in Table 2.

TABLE 2

| Fluoride Mixture | Temperature (° C.) | Products and Product Yields | | |
|---|---|---|---|---|
| | | 1,3-difluorobenzene | fluorobenzene | 1,2-difluorobenzene |
| $CuF_2$(5.0 g) + $AlF_3$ 1:2 | 500 | 5.4 | 63.1 | 3.4 |
| $CuF_2$(5.0 g) + $AlF_3$ 1:2 | 450 | 2.4 | 40.5 | 1.4 |
| $CuF_2$(5.0 g) + $AlF_3$ 1:2 | 425 | — | 23.8 | — |

From the powder X-ray analysis of the inorganic residue, reduction of $CuF_2$ to metallic copper was observed.

Introducing the benzene in fractions tested the consistency of reactivity of the fluoride bed. The results are given in Table 3.

TABLE 3

| Fluoride mixture | Benzene (ml) | Temperature (° C.) | Products | | |
|---|---|---|---|---|---|
| | | | 1,3-difluorobenzene | fluorobenzene | 1,2-difluorobenzene |
| $CuF_2$(5.0 g) + $AlF_3$ 1:2 | 0.5 | 500 | 7.2 | 65.8 | 3.8 |
| | 0.5 | 500 | 5.0 | 63.0 | 3.4 |
| | 0.5 | 500 | 2.9 | 52.6 | 2.5 |
| | 0.5 | 500 | — | 34.9 | 1.2 |
| $CuF_2$(5.0 g) + $AlF_3$ 1:2 | 0.5 | 425 | — | 27.9 | — |
| | 0.5 | 425 | — | 22.0 | — |
| | 0.5 | 425 | — | 19.9 | — |
| | 0.5 | 425 | — | 17.0 | — |

EXAMPLE 2

Fluorination of Benzene Utilizing $AlF_3$ and $MF_2$ (M=Ca, Zn, Mg) as the Fluorinating Agent Additional fluorination experiments using other materials such as $CaF_2$, $ZnF_2$, $MgF_2$ and activated carbon as additives were carried out. When benzene was treated with the activated carbon added copper fluoride, no fluorination was observed. The experimental conditions as mentioned in Example 1 were followed and the results are presented in Table 4.

TABLE 4

| Additives | Temperature (° C.) | Products | | |
|---|---|---|---|---|
| | | 1,3-difluorobenzene | fluorobenzene | 1,2-difluorobenzene |
| $CaF_2$ | 500 | 6.1 | 51.2 | 3.1 |
| $MgF_2$ | 500 | 4.6 | 44.0 | 2.6 |
| $ZnF_2$ | 500 | — | 38.2 | 1.7 |

EXAMPLE 3

Fluorination of Chlorobenzene

Fluorination of monochlorobenzene was carried out using $CuF_2$. Percentage conversion to fluorinated derivatives was improved by adding $AlF_3$ to $CuF_2$. The experimental conditions as mentioned in Example 1 were followed. Percentage conversions of chlorobenzene to the fluorinated products for differing $CuF_2$ and $AlF_3$ ratios are given in Table 5.

TABLE 5

| Fluoride Mixture | Temperature °C. | 1,3-F,F | benzene | F | 1,2-F,F | Cl,F (meta) | Cl,F (ortho) |
|---|---|---|---|---|---|---|---|
| $CuF_2$ (5.0 g) | 500 | 2.2 | 7.4 | 29.9 | 0.7 | 2.9 | 4.1 |
| $CuF_2$ (3.5 g) + $AlF_3$ 1:1 | 500 | 3.8 | 9.7 | 35.0 | 0.8 | 2.8 | 3.4 |
| $CuF_2$ (3.5 g) + $AlF_3$ 1:1.5 | 500 | 2.7 | 9.6 | 40.5 | 0.7 | 2.3 | 3.7 |
| $CuF_2$ (3.5 g) + $AlF_3$ 1:2 | 500 | 4.1 | 12.2 | 55.2 | 0.9 | 2.4 | 3.4 |
| $CuF_2$ (3.5 g) + $AlF_3$ 1:2.5 | 500 | 4.3 | 13.3 | 51.7 | 1.0 | 3.4 | 4.0 |
| $CuF_2$ (3.5 g) + $AlF_3$ 1:3 | 500 | 3.2 | 9.9 | 48.3 | 0.8 | 3.1 | 4.3 |

On the basis of the above results the ratio of $CuF_2$ to $AlF_3$ was fixed as 1:2, and additional experiments were carried out at 450° C., 425° C. and 400° C. The results are given in Table 6.

TABLE 6

Products and Product Yields

| Fluoride Mixture | Temperature °C. | 1,3-F,F | benzene | F | 1,2-F,F | Cl,F (meta) | Cl,F (ortho) |
|---|---|---|---|---|---|---|---|
| $CuF_2$ (5.0 g) + $AlF_3$ 1:2 | 500 | 8.3 | 8.8 | 65.7 | 1.8 | 3.6 | 3.2 |
| $CuF_2$ (5.0 g) + $AlF_3$ 1:2 | 450 | 3.7 | 13.6 | 56.6 | — | 2.8 | 3.4 |
| $CuF_2$ (5.0 g) + $AlF_3$ 1:2 | 425 | 0.9 | 11.3 | 30.3 | — | 0.9 | — |
| $CuF_2$ (5.0 g) + $AlF_3$ 1:2 | 400 | — | 4.1 | 18.0 | — | — | — |

Reduction of copper fluoride to metallic copper and the formation of CuCl were observed from the powder X-ray analysis of the inorganic residue.

EXAMPLE 4

Fluorination of Monofluorobenzene

The experimental conditions as mentioned in Example 1 were followed. The percentage conversions of monofluorobenzene to difluoro derivatives are given in Table 7. Powder X-ray diffraction analysis indicated the reduction of copper fluoride to metallic copper on reaction with monofluorobenzene.

TABLE 7

| Fluoride Mixture | Temperature °C. | Products and Product Yields 1,3-difluorobenzene | 1,2-difluorobenzene |
|---|---|---|---|
| $CuF_2$(3.5 g) | 500 | 2.0 | 1.2 |
| $CuF_2$(5.0 g) | 500 | 6.9 | 2.8 |
| $CuF_2$(5.0 g) + $AlF_3$ 1:2 | 500 | 21.2 | 7.0 |

EXAMPLE 5

Fluorination of Chloroaromatics using AgF as the Fluorinating Agent

Fluorination of Chlorotoluenes

Experiments attempting to fluorinate chloroaromatics using AgF were carried out in exactly the same manner as those carried out with $CuF_2$ in Example 1. The product yields of a constant temperature fluorination of all the chlorotoluenes utilizing AgF as the fluorinating agent is shown in Table 8.

TABLE 8

| Reactants | Temp. °C | Product Yield % 2-fluorotoluene | 3-fluorotoluene | 4-fluorotoluene | difluorotoluene |
|---|---|---|---|---|---|
| 2-chlorotoluene + AgF (3.5 g) | 350 | 13.9 | 14.4 | 0.5 | 3.3 |
| 3-chlorotoluene + AgF (3.5 g) | 350 | 6.7 | 25.7 | 15 | 7.7 |
| 4-chlorotoluene + AgF (3.5 g) | 350 | 0.6 | 35.8 | 20.8 | 3.9 |

Attempts to flourinate the resulting fluoroaromatic products listed in Table 1 yielded only a small increase in total fluoronation. The increased fluorination is shown in Table 9 for flourobenzene and flurotoluene.

TABLE 9

| Reactants | Temperature ° C. | Product Yields |
|---|---|---|
| fluorobenzene | 350 | Only 2–4% fluorination |

TABLE 9-continued

| Reactants | Temperature ° C. | Product Yields |
|---|---|---|
| 3-fluorotoluene | 350 | |

Fluorination of Dichlorobenzenes

All three dichlorobenzenes were fluorinated using the methods disclosed in Example 1. The fluorinating agent utilized was AgF and the four resulting product yields are shown in Table 10.

TABLE 10

| Reactants | Temp. ° C. | Product Yields % 1,3-difluorobenzene | 1,2-chlorofluorobenzene | 1,3-chlorofluorobenzene | 1,4-chlorofluorobenzene |
|---|---|---|---|---|---|
| 1,2-dichlorobenzene + AgF (3.5 g) | 350 | 12.2 | 2.5 | 4.2 | — |
| 1,3-dichlorobenzene + AgF (3.5 g) | 350 | 20.4 | 3.8 | 5.7 | 5.0 |
| 1,4-dichlorobenzene + AgF (3.5 g) | 350 | 1.4 | — | 3.4 | 4.2 |

Fluorination of Chlorofluorobenzenes

Fluorination of the three chlorofluorobenzenes as shown in the product yields in Table 11 selectively result in conversion to meta-fluorobenzene. The product yields of this fluorination reaction are shown in Table 11.

TABLE 11

| Reactants | Temperature °C. | Products and Product Yields % |
|---|---|---|
| 2-fluorochlorobenzene + AgF | 350 | 1,3-difluorobenzene 20.3 |
| 3-fluorochlorobenzene + AgF | 350 | 1,3-difluorobenzene 39.6 |
| 4-fluorochlorobenzene + AgF | 350 | 1,3-difluorobenzene 5.9 |

Fluorination of 2-Chloropyridine

Fluoroaromatics other than fluorobenzenes can also be fluorinated utilizing the process of the present invention. As the following schematic shows, a pyridine can be fluorinated with AgF to yield a fluorinated pyridine.

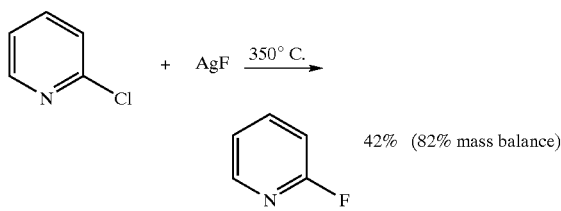

42% (82% mass balance)

We claim:

1. A method of fluorinating an aromatic compound or chloroaromatic compound comprising the steps of:
   a) mixing at least one active fluorinating agent selected from the group consisting of $CuF_2$, AgF, $HgF_2$, $TeF_4$, $MnF_4$, $FeF_3$, and $CoF_{2-4}$ with at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$;
   b) heating said mixture at a temperature of at least 300° C. or 350° C.; and
   c) contacting said mixture with an aromatic compound, a chloroaromatic compound, a mixture of aromatic compounds, a mixture of chloroaromatic compounds, or a mixture of chloroaromatic and aromatic compounds.

2. The method according to claim 1, wherein said method further comprises recovering fluorinated aromatic or chloroaromatic compounds.

3. The method according to claim 1, wherein said temperature is at least 400° C.

4. The method according to claim 1, wherein said temperature is at least 425° C.

5. The method according to claim 1, wherein said temperature is at least 450° C.

6. The method according to claim 1, wherein said temperature is at least 500° C.

7. The method according to claim 1, wherein said aromatic or chloroaromatic compound is selected from the group consisting of benzene, chlorobenzene, substituted benzene, substituted chlorobenzene, pyridines, chloropyridines, substituted pyridines, substituted chloropyridines, naphthalene, substituted naphthalenes, chloronaphthalene, substituted chloronaphthalenes, toluene, chlorotoluene, substituted toluene, and substituted chlorotoluene.

8. The method according to claim 1, wherein aromatic compounds are contacted with said mixture.

9. The method according to claim 1, wherein chloroaromatic compounds are contacted with said mixture.

10. The method according to claim 1, wherein a mixture of chloroaromatic and aromatic compounds are contacted with said mixture.

11. The method according to claim 9, wherein said mixture comprises AgF and at least one support.

12. The method according to claim 8, wherein said aromatic compounds are aromatic hydrocarbons.

13. The method according to claim 12, wherein said aromatic compounds are contacted with a mixture comprising $CuF_2$ and at least one support.

14. The method according to claim 9, wherein said chloroaromatic compound is ortho-dichlorobenzene, para-dichlorobenzene, meta-dichlorobenzene, a chloropyridine, chloronapthalene, a chlorpyridine, chlorotoluene, substituted ortho-dichlorobenzene, substituted para-dichlorobenzene, substituted meta-dichlorobenzene, a substituted chloropyridine, substituted chloronapthalene, a substituted chlorpyridine, substituted chlorotoluene, or mixtures thereof.

15. The method according to claim 14, wherein said chloroaromatic compound is contacted by a mixture comprising AgF and at least one support.

16. The method according to claim 12, wherein said aromatic compounds are contacted with a mixture consisting of $CuF_2$ and at least one support.

17. The method according to claim 11, wherein said mixture further comprises $CuF_2$.

18. The method according to claim 13, wherein said mixture further comprises AgF.

19. A method of fluorinating an aromatic compound comprising combining an aromatic compound, a chloroaromatic compound, a mixture of aromatic compounds, a mixture of chloroaromatic compounds, or a mixture of chloroaromatic and aromatic compounds and a fluorinating composition comprising at least one active fluorinating agent selected from the group consisting of $CuF_2$, AgF, $HgF_2$, $TeF_4$, $MnF_4$, $FeF_3$, and $CoF_{2-4}$ and at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$ and heating the combined components a temperature of at least 350° C.

20. The method according to claim 5, wherein said mixture comprises one part active fluorinating agent and one part to three parts of the at least one support.

21. The method according to claim 20, wherein the active fluorinating agent is $CuF_2$ and at least one support is $AlF_3$.

22. The method according to claim 5, wherein said mixture comprises one part active fluorinating agent and two parts of the at least one support.

23. The method according to claim 22, wherein the active fluorinating agent is $CuF_2$ and at least one support is $AlF_3$.

24. The method according to claim 6, wherein said mixture comprises one part active fluorinating agent and one part to three parts of the at least one support.

25. The method according to claim 6, wherein said mixture comprises one part active fluorinating agent and two parts of the at least one support.

26. The method according to claim 24, wherein the active fluorinating agent is $CuF_2$ and at least one support is $AlF_3$.

27. The method according to claim 25, wherein the active fluorinating agent is $CuF_2$ and at least one support is $AlF_3$.

28. A method for producing a fluorinated aromatic or chlorofluoro aromatic compound comprising:
   a) mixing at least one active fluorinating agent selected from the group consisting of $CuF_2$, $AgF$, $HgF_2$, $TeF_4$, $MnF_4$, $FeF_3$, and $CoF_{2-4}$ with at least one support selected from the group consisting of activated carbon, $ZnF_2$, $CaF_2$, $MgF_2$, $AlF_3$, and combinations of activated carbon, $ZnF_2$, $CaF_2$, $MgF_2$, or $AlF_3$;
   b) heating said mixture at a temperature of at least 450° C.; and
   c) contacting said mixture with an aromatic compound, a chloroaromatic compound, a mixture of aromatic compounds, a mixture of chloroaromatic compounds, or a mixture of chloroaromatic and aromatic compounds.

29. The method according to claim 28, wherein the temperature is at least 500° C.

30. The method according to claim 28, wherein said aromatic or chloroaromatic compound is selected from the group consisting of benzene, chlorobenzene, substituted benzene, substituted chlorobenzene, pyridines, chloropyridines, substituted pyridines, substituted chloropyridines, naphthalene, substituted naphthalenes, chloronaphthalene, substituted chloronaphthalenes, toluene, chlorotoluene, substituted toluene, and substituted chlorotoluene.

31. The method according to claim 28, wherein said mixture comprises one part active fluorinating agent and one part to three parts of the at least one support.

32. The method according to claim 31, wherein the active fluorinating agent is $CuF_2$ and at least one support is $AlF_3$.

33. The method according to claim 28, wherein said mixture comprises one part active fluorinating agent and two parts of the at least one support.

34. The meted according to claim 33, wherein the active fluorinating agent is $CuF_2$ and at least one support is $AlF_3$.

35. The method according to claim 32, wherein the support is $AlF_3$.

36. The method according to claim 34, wherein the support is $AlF_3$.

37. The method according to claim 28, wherein said method further comprises recovering fluorinated aromatic or chlorofluoroaromatic compounds.

* * * * *

UNITED STATES PATENT AND TRADEMARK OFFICE
CERTIFICATE OF CORRECTION

PATENT NO. : 7,012,165 B2
APPLICATION NO. : 10/698110
DATED : March 14, 2006
INVENTOR(S) : William R. Dolbier, Jr. and Buvaneswari Gopal It is certified that error appears in the above-identified patent and that said Letters Patent is hereby corrected as shown below:

Title page,
Item (74), "& Salinwanchik" should read --& Saliwanchik--.

Column 3,
Line 20, "$Hg_2F_2$. As illustrated" should read
   --$Hg_2F_2$.
      As illustrated--.

Column 3,
Line 29, "fluorbenzene: diflorobenzene" should read --fluorobenzene: diflorobenzene--.

Column 4,
Line 41, "flurobenzene" should read --fluorobenzene--.

Column 11,
Line 1, "flourinate" should read --fluorinate--.
Line 3, "fluoronation" should read --fluorination--.
Line 4, "flourobenzene" should read --fluorobenzene--.
Line 4, "flurotoluene" should read --fluorotoluene--.

Column 12,
Lines 5-10, Table 9,

"
| Reactants | Temperature °C | Product Yields |
|---|---|---|
| [structure: fluorotoluene] | 350 | |
"

should read

--
| Reactants | Temperature °C | Product Yields |
|---|---|---|
| [structure: fluorotoluene] | 350 | Only 2-4% fluorination |
--

UNITED STATES PATENT AND TRADEMARK OFFICE
CERTIFICATE OF CORRECTION

PATENT NO. : 7,012,165 B2
APPLICATION NO. : 10/698110
DATED : March 14, 2006
INVENTOR(S) : William R. Dolbier, Jr. and Buvaneswari Gopal It is certified that error appears in the above-identified patent and that said Letters Patent is hereby corrected as shown below:

Column 15,
Line 3, "components a temperature" should read --components at a temperature--.

Signed and Sealed this

Third Day of October, 2006

JON W. DUDAS
*Director of the United States Patent and Trademark Office*